(12) United States Patent
Bürgel et al.

(10) Patent No.: US 6,852,018 B2
(45) Date of Patent: Feb. 8, 2005

(54) DEVICE FOR TESTING THE SCRATCH RESISTANCE OF SURFACES

(75) Inventors: Andreas Bürgel, Duisburg (DE);
Georg Lamp, Leverkusen (DE);
Robert Maleika, Düsseldorf (DE);
Leslaw Mleczko, Bochum (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/690,932

(22) Filed: Oct. 22, 2003

(65) Prior Publication Data

US 2004/0092215 A1 May 13, 2004

(30) Foreign Application Priority Data

Oct. 25, 2002 (DE) ......................................... 102 49 725

(51) Int. Cl.[7] ................................................. B24C 3/00
(52) U.S. Cl. ......................................... 451/75; 451/102
(58) Field of Search ............................. 451/75, 87, 78, 451/81, 89, 92, 84, 102, 96, 99; 73/7, 78, 81

(56) References Cited

U.S. PATENT DOCUMENTS

| | | | |
|---|---|---|---|
| 3,229,498 A | 1/1966 | Oakes | |
| 4,125,969 A | * 11/1978 | Easton | 451/39 |
| 4,319,436 A | * 3/1982 | Van Fossen | 451/87 |
| 5,099,619 A | * 3/1992 | Rose | 451/99 |
| 5,250,807 A | 10/1993 | Sontvedt | |
| 5,545,074 A | * 8/1996 | Jacobs | 451/40 |
| 5,740,863 A | 4/1998 | Ortloff et al. | |
| 2002/0135758 A1 | 9/2002 | Potyrailo et al. | |

FOREIGN PATENT DOCUMENTS

DE 2 013 693 10/1971

OTHER PUBLICATIONS

Patent Abstracts of Japan, vol. 009, no. 127 (P–360), May 31, 1985 & JP 60 010146 A (Shigenobu Takahashi), Jan. 19, 1985.
Patent Abstracts of Japan, vol. 007, no. 206 (P–222), Sep. 10, 1983 & JP 58 100742 A (Meidensha KK), Jun. 15, 1983.
ONORM M 8126, (month unavailable) 1989, pp. 1–4, "Tribotechnik".
J. Oil Colour Chem. Assocn. 11, (month unavailable) 1928, pp. 230–259, E.W. J. Mardles, "Some Methods of Testing the suitability of Paints, Varnishes, and Lacquers for Aeronautical Purposes".
Surface and Coatings Technology 71, (month unavailable) 1995, pp. 1–8, P.H. Shipway, L.M. Hutchings, "Measurement of coating durability by solid particle erosion".
DIN 52 348, Feb. 1985, pp. 1–4, "Verschleißprüfung".
DIN 52 347, Dec. 1987, pp. 1–6, "Verschleißprüfung".
ASTM G 76–95 (Reapproved 2000), pp. 1–5, "Standard Test Method for Conduction Erosion Tests by Solid Particle Impingement Using Gas Jets".

* cited by examiner

*Primary Examiner*—Dung Van Nguyen
(74) *Attorney, Agent, or Firm*—Joseph C. Gil; Gary F. Matz

(57) ABSTRACT

A device for testing the scratch resistance of a surface of a test specimen by means of a gas stream charged with solid particles, comprising:
  a tube, having an entry and an exit, for directing the gas stream on to a specimen holder with the surface to be tested,
  a means for providing the gas stream, and
  a metering device positioned along the tube for metering the solid particles into the gas stream,
wherein a tube part is angled at an angle in the region of the tube exit and the angled tube part has, at the angle, an opening at which the specimen holder is positioned such that the gas stream is directed on to the specimen holder.

16 Claims, 1 Drawing Sheet

DEVICE FOR TESTING THE SCRATCH RESISTANCE OF SURFACES

CROSS REFERENCE TO RELATED PATENT APPLICATION

The present patent application claims the right of priority under 35 U.S.C. §119 (a)–(d) of German Patent Application No. 102 49 725.7, filed Oct. 25, 2002.

FIELD OF THE INVENTION

The invention relates to a device for testing the scratch resistance of surfaces. Testing of the scratch resistance is carried out by means of a gas stream charged with solid particles which flows over the surface to be tested. The device is used in particular for simulation, under conditions close to those in practice, of the scratching processes on automobiles in the relative wind when driven through dirt particles, drift sand or the like.

BACKGROUND OF THE INVENTION

Various, in some cases standardized methods for testing the scratch resistance of surfaces are known from the prior art. All these processes have the common feature that the surfaces of test specimens are scratched by a contacting relative movement by solids of high hardness either with several contact points, for example by loose or bound particles, or with only one contact point, for example a diamond tip. With all the methods described, as a rule the optical and/or topographical properties of the surface are analyzed after the scratching of the surfaces. This is carried out e.g. by measurement of the optical haze or of the gloss or by examinations under a light, scanning electron or atomic microscope.

The standardized methods for testing the scratch resistance include the sand trickling method (DIN 52 348). In the sand trickling method, the surface of a test specimen is scratched by a well-defined standard sand which falls through a fall pipe from a height of 1,650 mm. The amount of sand is specified here as 3 kg. The impact speed of the sand results directly from the height of fall (ignoring air friction) as 5.69 m/s. However, in respect in particular of simulation of the exposure of the surfaces of vehicle components to abrasion in the relative wind due to drift sand, dirt particles or the like, the impact speed of the sand trickling method is too low. The impact speed of particles in the relative wind is usually between about 30 km/h and 200 km/h, i.e. between 8.33 m/s and 55.56 m/s.

Another standardized test method is the abrasive disc method, also called the Taber Abraser test (DIN 52 347). In the Taber Abraser test, the surfaces of the test specimens, which lie on the rotary plate of the abrasion tester, are exposed to sliding wear by two abrasive discs rotating in the opposite direction. The abrasive discs of Teledyne Taber (USA), type CS 10 F are made of a defined fine-grained abrasive embedded in rubber. For simulation of the exposure of the surfaces of vehicle components to abrasion in the relative wind by drift sand, dirt particles or the like, the Taber Abraser test has the disadvantage that the contact force of the abrading medium on the test specimens, either 2.7 N or 5.4 N, is too high compared with the range relevant to automobile applications. Model estimations of the contact force of particles in the relative wind give values of about 0.5 N. Furthermore, this contact force occurs only over a period of less than 1 $\mu$s.

E. W. J. Mardles, *J. Oil Colour Chem. Assocn.* (1928), 11, pages 230–259 and P. H. Shipway and I. M. Hutchings, *Surface and Coatings Technology* (1995), 71(1), pages 1–8 describe methods in which abrasive particles are blasted on to a specimen surface by a stream of air. With these methods comparatively high relative speeds between the abrading medium and specimen surface of up to 77 m/s indeed arise. However, a disadvantage of these methods is that the angle of incident flow cannot be varied. In the methods described in the standards ASTM G 76-95 and ÖNORM M 8126, a stream of particles is likewise directed on to a surface at a high speed. However, all these methods have the common feature that the exit of the nozzle tube or the like which guides the gas particle stream to the specimen surface is at a distance from the test specimen, which is held freely in space. This means that the gas particle stream flows freely between the exit of the nozzle tube and the specimen surface, which can lead to swirling and turbulence in the region of the specimen surface. A well-defined flow and therefore a reproducible exposure of the specimen surface to scratching thus does not exist.

The object of the present invention was to provide a device for testing the scratch resistance of surfaces which does not have the disadvantages mentioned. The object is achieved according to the invention by the features of claim 1.

SUMMARY OF THE INVENTION

The present invention is directed to a device for testing the scratch resistance of a surface of a test specimen by means of a gas stream charged with solid particles, comprising:

a tube, having an entry and an exit, for directing the gas stream on to a specimen holder with the surface to be tested, a means for providing the gas stream, and a metering device positioned along the tube for metering the solid particles into the gas stream, wherein a tube part is angled at an angle in the region of the tube exit and the angled tube part has, at the angle, an opening at which the specimen holder is positioned such that the gas stream is directed on to the specimen holder.

DETAILED DESCRIPTION OF THE INVENTION

Figure 1:
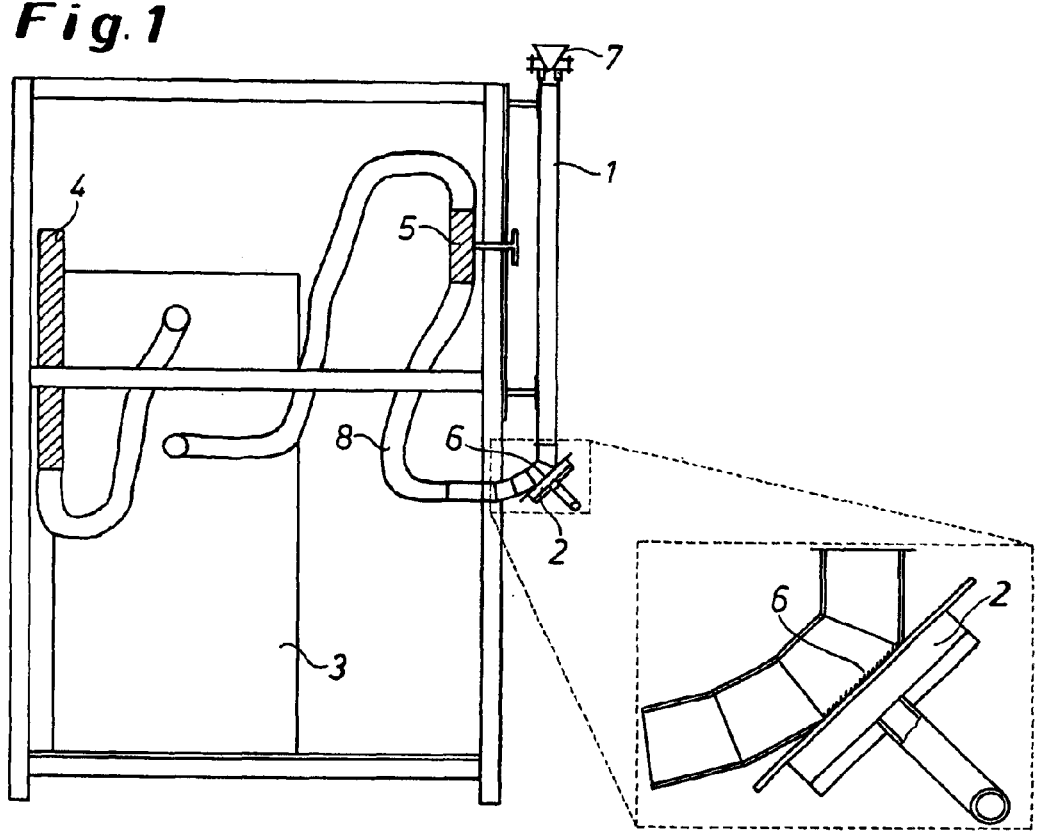
FIG. 1 shows a front elevation view of a device according to the invention.

Other than in the operating examples, or where otherwise indicated, all numbers or expressions referring to quantities of ingredients, reaction conditions, etc. used in the specification and claims are to be understood as modified in all instances by the term "about."

The invention provides a device for testing the scratch resistance of surfaces of a test specimen by means of a gas stream charged with solid particles, at least comprising a tube, which is replaceable, for directing the gas stream on to a specimen holder with the surface to be tested, a fan at the tube entry or a suction device at the tube exit being provided for generation of the gas stream, and a metering device at the tube entry or downstream along the tube for metering the solid particles into the gas stream, wherein the tube is angled in the region of the tube exit and the angled tube part has, at the angle, an opening at which the specimen holder is connected detachably to the tube, or instead of the opening a specimen holder is provided at the angle inside the angled tube part, the opening with the specimen holder or the specimen holder inside the tube being positioned such that the gas stream is directed on to the specimen holder.

The specimen holder serves to attach the test surface to the lateral opening of the tube, which is at the angle in the angled part of the tube, i.e. in the direction of flow after the angle. The lateral opening is positioned here such that the gas stream is directed on to the specimen holder with the surface to be tested. Alternatively, it is also possible to provide a specimen holder inside the tube, this also being positioned such that the gas stream loaded with particles is directed on to the specimen holder. In this alternative no opening is provided at the angle.

The specimen holder can be e.g. a plate or a square stone on which the surface to be tested is placed or with the aid of which the specimen surface is pressed on to the tube opening. The specimen holder is accordingly connected detachably to the tube. It can be fixed, for example, with the aid of a screw or clamp connection or by springs by means of pressure or tension. The specimen holder can be attached to the opening in a reproducible manner in this way. If a suction device is used to generate the gas stream, the suction pressure can optionally be high enough to press the test object on to the opening, so that no additional fixing means are necessary.

The tube through which the gas stream charged with particles is led is replaceable, i.e. it is connected detachably to the other components of the device, in particular the metering device, the specimen holder and the suction device or the like which serves to generate the gas stream. This has the advantage that the tube can be replaced by another tube with a different angle by easy manipulation. The angle of incident flow under which the specimen surface is tested can be varied in this manner. The angle of the tube, and therefore the angle of incident flow, is preferably 5 to 90°.

The tube can have any desired cross-sections. Preferably, however, it has a square cross-section. The diameter of the tube is substantially constant over the entire length of the tube. To achieve a uniform flow profile, which is necessary for a scratching of the surface which is as homogeneous as possible and therefore for a high reproducibility, the ratio of the diameter to the length of the tube is a deciding factor, the length of the tube which is decisive for this being the distance between the metering device and the opening or the specimen holder with the test surface. The diameter of the tube and the length of the tube between the metering device and the opening are accordingly preferably in a ratio of 1:5 to 1:100, particularly preferably 1:20 to 1:30 to one another. In the case of a square cross-section, the diameter of the tube is to be understood as the edge length of the tube. By using a square cross-section in particular, changes in cross-section and therefore local changes in speed in the region of the angle, i.e. in the region of the specimen surface, can be avoided.

A particular advantage of the device according to the invention is that the specimen holder can be attached to the lateral opening in the region of the tube angle such that is covers the opening completely. The tube is therefore closed, with the exception of the openings at the entry and exit of the tube and, where appropriate, an additional opening for metering the solid particles into the gas stream. The specimen surface to be tested faces into the inside of the tube and is therefore shielded from the surroundings. If the tube were not connected to the specimen but directed on to the specimen at a distance, the gas stream would flow freely between the tube exit and the specimen. The flow profile of the gas stream would be distorted on discharge from the tube. Swirling would occur in the region of the specimen surface, and therefore an inhomogeneous scratching of the specimen surface.

The gas stream, e.g. a stream of air, is generated by increased pressure with the aid of a compressor, fan or the like or by reduced pressure with the aid of a vacuum pump. Solid particles can be added to the gas stream in a regulated or non-regulated manner, but preferably in a regulated manner over a certain period of time. This can be effected, for example, by a gravimetrically regulated metering device. However, for example, a funnel operating by the hour glass principle can also alternatively be used as the metering device. A control valve is attached to the tube for regulation of the flow rate. The flow rate of the gas stream charged with solid particles is preferably in the range from 1 to 100 m/s, particularly preferably 5 to 50 m/s. With a suitable choice of the suction device or the fan for generation of the gas stream, higher flow rates are also possible.

The device is suitable, for example, for testing surfaces of glass, metal, ceramic or a synthetic material, for example coatings. The materials mentioned can also serve as the substrate, which is provided with a coating to be tested of glass, metal, ceramic or a synthetic material, for example coatings.

Particles which can be employed are, for example, granular solids, e.g. of sand, metal or metal oxide. The particle size is preferably 10 to 2,000 $\mu$m. The density of the solid particles is preferably 500 to 22,000 kg/m$^3$, particularly preferably 1,000 to 10,000 kg/m$^3$.

Particle amounts of 1 to 10 g are conventionally metered into the gas stream. Depending on the nature of the particles and of the surface to be tested, however, any desired smaller or larger amounts can be employed. The loading of the gas stream with solid particles is preferably 0.1 to 500 g/m$^3$.

The invention is explained in more detail below with reference to the attached FIG. 1.

FIG. 1 shows a diagram of a preferred embodiment of the device according to the invention.

A stream of air generated with the aid of a suction unit 3 flows through the square tube 1 with an inner edge length of 36 mm. A well-defined weight of sand or the like is fed via a funnel 7 at the upper end of the vertically arranged tube 1. The funnel 7 has a height of 50 mm and a discharge opening of 2 mm at an opening angle of 40°. The funnel is positioned over the entry opening of the tube 1 by spacers, so that air can flow into the tube opening from the side. The width of the gap through which the air enters from the side and therefore the speed can be varied by varying the height of the spacers. As a result, mixing of the particles into the stream of air can be optimized, where appropriate, such that a distribution which is as homogeneous as possible is achieved by turbulence of the stream of air in the tube entry region.

In the embodiment shown in FIG. 1 the vertically arranged tube 1 has at the lower end an angle of 45°, on which is an opening 6. The opening 6 with a size of 57×34 mm is, in particular, below the angle, i.e. in the direction of flow after the angle, on the outer side of the square tube 1. A specimen holder 2 is attached to the tube at the opening 6. The opening 6 with the specimen holder 2 is therefore positioned on the angle such that the gas stream is directed on to the specimen. The specimen holder 2 is, in particular, connected detachably to the tube 1. In the embodiment shown the specimen holder 2 is a plate which is pressed e.g.

with the aid of spiral springs on to the opening of the tube. The surface to be tested, which is on the specimen holder 2, faces into the inside of the tube 1 in this arrangement and thus forms an inner surface of the tube at the opening 6. The stream of air charged with particles therefore flows to the specimen surface under a defined angle of 45°. The tube 1 is connected detachably to the waste air hose 8 or the like. In particular, the tube 1 is connected to the waste air hose 8 with the aid of screw or flange connections. This enables the tube 1 to be replaced by a tube with a different angle in a simple manner. The length of the vertically arranged tube part, and therefore the length of the tube between the metering device 7 and opening 6 or specimen holder 2, is 1 m.

The volume flow and therefore the flow rate is regulated with the aid of a control valve 5 attached on the waste air hose 8 in the embodiment shown. The particles with which the stream of air has been charged are separated off by a cyclone and by filters in the suction unit 3. The flow rate of the waste air cleaned in this way is recorded by a thermal flow sensor 4.

EXAMPLE

Test specimens with a surface of polycarbonate of the type Makrolon® from Bayer were tested for their scratch resistance with the aid of the device shown in FIG. 1. The surface was not additionally coated with a scratch-resistant layer. The test specimens had a size of 40×60 mm at a thickness of 2 mm. The opening of the tube was 34×57 mm, which corresponds to the area of the test surface. Quartz sand with a particle size distribution of 125 to 250 $\mu$m was used as the solid particles. 3.5 g of quartz sand with a density of 1,500 kg/m$^3$ were metered into the stream of air with the aid of a funnel with a height of 50 mm and a discharge opening of 2 mm at an opening angle of 40°. The time span in which the quartz sand trickled via the funnel into the tube was—also depending on the flow rate chosen for the stream of air—a maximum of 15 s. This corresponds to the duration of the exposure of the test surface to abrasion.

The length of the tube between the tube entry opening with the metering device and the specimen surface was 1 m. The tube internal edge length was 36 mm. The angle of incident flow was 45°. The stream of air was generated with the aid of a suction unit.

In each case 3 specimen surfaces were tested with incident flow rates of 10, 20, 30 and 40 m/s, in order to test the reproducibility of the experiments. The loading of the stream of air with particles was 18 g/m$^3$ at 10 m/s, 9 g/m$^3$ at 20 m/s, 6 g/m$^3$ at 30 m/s and 4.5 g/m$^3$ at 40 m/s.

After the surface had been scratched, the optical haze was measured with the aid of a haze meter from HunterLab, model D25D2P in accordance with the standard ASTM D1003-95. In this procedure, a hazed transparent specimen was transilluminated by a parallel bundle of light and the content of light scattered diffusely by the specimen was determined in comparison with the total intensity. In these measurements a circular cut-out of the specimen surface was investigated with a light bundle of 25 mm diameter.

The measurement results are summarized in table 1. The optical haze in % corresponds to the content of light scattered diffusely through the specimen in comparison with the total intensity of the light. The dependence of the optical haze on the flow rate is clearly to be seen, the measurement values being very readily reproducible. The relative standard deviation is less than 2.3%.

TABLE 1

Optical haze as a function of the incident flow rate

| Flow rate [m/s] | Optical haze [%] | Relative standard deviation [%] |
|---|---|---|
| 10 | 5.4 | 1.85 |
| 10 | 5.3 | |
| 10 | 5.5 | |
| 20 | 12 | 0.83 |
| 20 | 12.2 | |
| 20 | 12.1 | |
| 30 | 18.4 | 1.64 |
| 30 | 18.6 | |
| 30 | 19 | |
| 40 | 26.1 | 2.28 |
| 40 | 25 | |
| 40 | 25.9 | |

To test the homogeneity of the scratching, additional measurements of the optical haze were carried out on a specimen which was scratched at an incident flow rate of 40 m/s and an incident flow angle of 45°, the diameter of the light bundle being reduced to 10 mm with the aid of an aperture. This enables smaller cut-outs of the specimen surface to be transilluminated, lower haze values occurring due to the measurement technique.

On the specimen surface of 34×57 mm, the optical haze was measured at 12 measurement points in the form of a 3×4 matrix. The measurement values are summarized in table 2. The measurements show the high homogeneity of the scratching on the surface tested. The relative standard deviation was 1.83%.

TABLE 2

Optical haze at various measurement points on the test surface

| Measurement point | x, mm | y, mm | Optical haze, % | Relative standard deviation, % |
|---|---|---|---|---|
| 1 | 5 | 5 | 10.8 | 1.83 |
| 2 | 15 | 5 | 10.7 | |
| 3 | 25 | 5 | 10.6 | |
| 4 | 35 | 5 | 10.9 | |
| 5 | 5 | 15 | 11.3 | |
| 6 | 15 | 15 | 10.7 | |
| 7 | 25 | 15 | 10.9 | |
| 8 | 35 | 15 | 10.8 | |
| 9 | 5 | 25 | 10.9 | |
| 10 | 15 | 25 | 10.6 | |
| 11 | 25 | 25 | 10.6 | |
| 12 | 35 | 25 | 10.9 | |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A device for testing the scratch resistance of a surface of a test specimen by means of a gas stream charged with solid particles, comprising a tube, having an entry and an exit, for directing the gas stream on to a specimen holder with the surface to be tested, a means for providing the gas stream, and a metering device positioned along the tube for metering the solid particles into the gas stream, wherein a tube part is angled at an angle in the region of the tube exit and the angled tube part has, at the angle, an opening at which the specimen holder is positioned such that the gas stream is directed on to the specimen holder.

2. The device according to claim 1, characterized in that the angle of the tube in the region of the opening is 5 to 90°.

3. The device according to claim 1, characterized in that the diameter of the tube and the length of the tube between the metering device and the opening are in a ratio of 1:5 to 1:100 to one another.

4. The device according to claim 3, wherein the diameter of the tube and the length of the tube between the metering device and the opening are in a ratio of 1:20 to 1:30 to one another.

5. The device according to claim 1, characterized in that the tube has a square cross-section.

6. The device according to claim 1, characterized in that the tube has a control valve for regulation of the flow rate.

7. The device according to claim 1, characterized in that the flow rate of the gas stream charged with solid particles can be regulated in the range from 1 to 100 m/s.

8. The device according to claim 1, characterized in that the particle size of the solid particles is from 10 to 2,000 $\mu$m.

9. The device according to claims 1, characterized in that the density of the solid particles is from 500 to 22,000 $kg/m^3$.

10. The device according to claims 9, wherein the density of the solid particles is from 1,000 to 10,000 $kg/m^3$.

11. The device according to claim 1 characterized in that the loading of the gas stream with solid particles is from 0.1 to 500 $g/m^3$.

12. The device according to claim 1, wherein the means for providing the gas stream includes one or both of a fan at the tube entry and a suction device at the tube exit.

13. The device according to claim 1, wherein the tube is replaceable.

14. The device according to claim 1, wherein the specimen holder is connected detachably to the tube.

15. The device according to claim 1, wherein the specimen holder is provided at the angle inside the angled tube part.

16. The device according to claim 1, wherein the solid particles comprise one or more particles selected from sand, metal and metal oxide.

* * * * *